US00PP33582P2

(12) United States Plant Patent
Hansen

(10) Patent No.: US PP33,582 P2
(45) Date of Patent: Oct. 26, 2021

(54) ***ECHINACEA* PLANT NAMED 'FRANKLY SCARLET'**

(50) Latin Name: ***Echinacea* hybrid**
Varietal Denomination: Frankly Scarlet

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 32 days.

(21) Appl. No.: 17/300,047

(22) Filed: Feb. 23, 2021

(51) Int. Cl.
*A01H 5/02* (2018.01)
*A01H 6/14* (2018.01)

(52) U.S. Cl.
USPC ..... Plt./428
CPC ..... *A01H 6/1448* (2018.05)

(58) Field of Classification Search
USPC ..... Plt./428
CPC ..... A01H 6/1448; A01H 5/02
See application file for complete search history.

*Primary Examiner* — Keith O. Robinson

(57) ABSTRACT

The new and distinct cultivar of *Echinacea* plant named 'Frankly Scarlet', with fragrant inflorescences on strong well-branched stems above dark green foliage. The inflorescences produce single whorls of broadly-overlapping, long, broad, scarlet-orange, ray florets that lighten with maturity to coral-orange. The new plant is vigorous and produces a compact habit and flowers from mid-summer to fall frost. The new plant is attractive and suitable as a potted plant, fur the landscape, and for cut flower arrangements.

1 Drawing Sheet

Botanical denomination: *Echinacea* hybrid.
Cultivar designation: 'Frankly Scarlet'.

STATEMENT REGARDING PRIOR DISCLOSURES UNDER 37 CFR 1.77(B)(6)

The first non-enabling disclosure of the claimed plant, in the form of a photograph and brief description was on a website operated by Walters Gardens, Inc. on Dec. 1, 2019. *Echinacea* 'Frankly Scarlet' was also listed with a photograph and brief description in the "Walters Gardens 20-21 Catalog" distributed first on May 20, 2020. The claimed plant was first sold on Mar. 2, 2020 by Walters Gardens, Inc., who obtained the plant and all information relating thereto, from the inventor. No plants of *Echinacea* 'Frankly Scarlet' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to the new and distinct cultivar of Coneflower from the genus *Echinacea* and given the cultivar name 'Frankly Scarlet'. The new plant was the result of a cross on Aug. 8, 2016 by the inventor between the proprietary unreleased hybrid known only by the breeder code 15-29-12 (not patented) and the proprietary unreleased hybrid known only by the breeder code as 15-29-13 (not patented) at a wholesale perennial nursery in Zeeland, Mich. This single seedling selected was evaluated first in trials in the summer of 2017 at the same nursery and assigned the breeder code of 16-86-12. *Echinacea* 'Frankly Scarlet' has been asexually propagated at the same nursery by basal crown division since 2017 and also using careful shoot tip tissue culture procedures and found to reproduce plants that exhibit all the characteristics identical to the original plant.

*Echinacea* 'Frankly Scarlet' is distinct from all other Coneflowers known to the inventor. The nearest comparison cultivars are: 'Solar Flare' U.S. Plant Pat. No. 22,133, 'Balsomsed' U.S. Plant Pat. No. 23,105, 'Balsomanita' U.S. Plant Pat. No. 30,138, 'Fourth of July' U.S. Plant Pat. No. 26,075 and 'Tomato Soup' U.S. Plant Pat. No. 19,427.

The female parent plant, 15-29-12, was taller with less branching habit, with less overlapping ray petals of more orangish color. The male parent plant, 15-29-13 was taller with less branching habit, with less overlapping ray petals of more orangish color. Further comparison with the parents is not possible as neither plants nor photography of the parents were maintained.

'Solar Flare' has larger inflorescences on taller plants, with narrower ray florets that are more purplish-red. 'Balsomsed' is shorter in habit, the inflorescences are smaller, the ray florets are more vivid red when first opening and less pinkish when mature and the foliage is not as dark green. 'Balsomanita' is smaller in habit, slightly smaller inflorescences with ray florets of dark purplish-red. 'Fourth of July' has smaller inflorescences on smaller plants and the ray petals are a purplish-red. 'Tomato Soup' has a slightly taller habit, the inflorescences have fewer ray florets with less overlapping.

SUMMARY OF THE INVENTION

*Echinacea* 'Frankly Scarlet' has not been evaluated under all possible environmental conditions. The phenotype may vary with variations in environment including: temperature, available sunlight intensity and duration, nutrients, water, etc. without a change in the genotype of the plant. The new plant is distinct from its parents and all other *Echinacea* known to the applicant in the following combined traits:

1. Large, broad, fragrant inflorescences with single whorl of ray florets that stay mostly horizontal once open;
2. Ray petals are wide and broadly-overlapping;
3. Ray petals are bright scarlet-orange and lighten with age to coral-orange;
4. Vigorous growth and excellent habit with good branching;
5. Large, dark-green, lanceolate foliage.

BRIEF DESCRIPTION OF THE DRAWINGS

The photographs of 'Frankly Scarlet' demonstrate the overall appearance of the plant including the unique traits. The drawings of the new plant are of a two-year-old plant grown in full-sun trial garden in Zeeland, Mich. The colors are as accurate as reasonably possible with color reproductions. Some slight variation of color may occur as a result of lighting quality, intensity, wavelength, direction or reflection.

DETAILED DESCRIPTION OF THE PLANT

Figure 1:
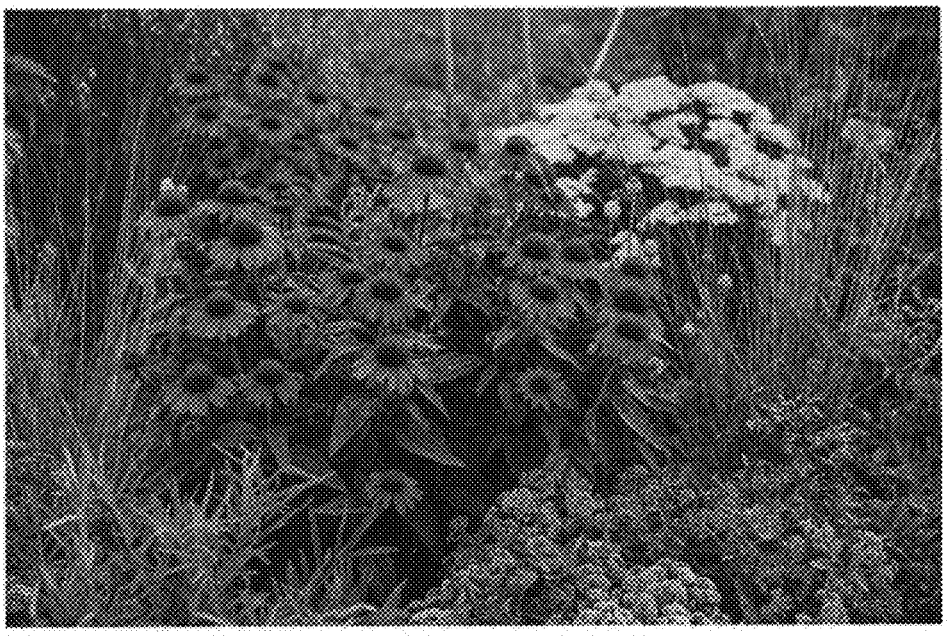
FIG. 1 shows the habit of the new plant in flower.
Figure 2:
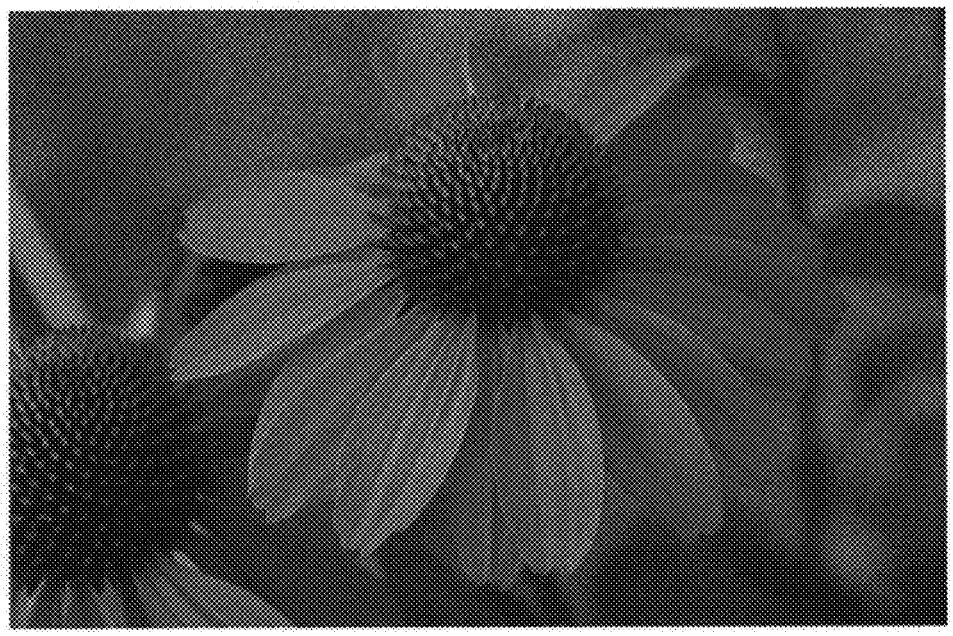
FIG. 2 shows a close up of some inflorescences of the new plant.

The following description of *Echinacea* 'Frankly Scarlet' is based on observations of two-year-old specimens grown in a full-sun trial garden with supplemental water and fertilizer in Zeeland, Mich. The new plant has not been tested in all environments and some phenotypic differences may occur with different environments without, however, any change in genotype. The color descriptions are based on the 2015 edition of The Royal Horticultural Society Colour Chart except where common dictionary descriptions are used.

Parentage: The female or seed parent is the proprietary unreleased hybrid 15-29-12 and the male or pollen parent is the proprietary unreleased hybrid 15-29-13; The parents are a complex set of crosses including 'Solar Flare', 'Little Annie' (not patented) and 'Butterfly Kisses' U.S. Plant Pat. No. 24,458.

Plant habit: Multi-stemmed, heavily-branched, hardy herbaceous perennial, flowering to about 70.0 cm tall and 54.0 cm wide;

Growth rate: Vigorous, finishing in 4 liter containers in about 2 months during the summer;

Roots: Cream-colored, finely branched; color nearest RHS NN155B depending on soil;

Foliage: Alternate; lanceolate; acute apex; attenuate base; margin serrulate, micro-ciliolate; puberulent abaxial and adaxial; to about 12.0 cm long and 5.0 cm wide decreasing distally, average about 9.5 cm long and 3.8 cm wide; variegation absent;

Leaf color: Young leaves adaxial between RHS 144A and RHS 146D, abaxial nearest RHS 147B; mature leaves adaxial between RHS 139A and RHS NN137A, abaxial nearest RHS 137B;

Foliage fragrance: Lightly herbal;

Venation: Pinnate; with two primary arcuate veins on both sides of the midrib; abaxial midrib and veins costate; glabrous adaxial, sparsely hirsutulous abaxial;

Vein color: Young and mature adaxial primary veins and midrib between RHS 148D and RHS 145C, primary veins nearest RHS 145A; young abaxial midrib nearest RHS 148D and primary veins nearest RHS 147C; mature adaxial midrib nearest RHS 148C, primary veins nearest RHS NN137A; mature abaxial midrib nearest RHS 148C, primary veins nearest RHS 147A;

Petiole: Concavo-convex, strigillose adaxial and sparsely puberulent to strigillose abaxial; to about 6.0 cm long and 3.0 mm wide on lowest leaves and decreasing in length to nearly sessile distally; adaxial color nearest RHS 148D in center with margins between RHS 139A and RHS NN137A, and abaxial center nearest RHS 148C with margins nearest RHS 137B;

Peduncle: Densely puberulent to strigillose; cylindrical; strong stiff; to about 68.0 cm long and 9.0 mm diameter at base; quantity per plant about ten; flowering in upper 24.0 cm;

Peduncle color: Between RHS 146A and RHS 137B;

Branches: Cylindrical, puberulent to strigillose; tightly angled to main stem to about 65° above horizontal: to about 28.0 cm long and 5.0 mm diameter; color between RHS 146A and RHS 137B;

Inflorescence: Bracteate head, aggregate of achene; with single whorl of distinct, imbricate, ligulate, ray florets and central disk florets in a pappus; flowering mid-summer to fall frost; initial inflorescence largest, to about 10.2 cm wide and 4.5 cm tall, average about 9.0 cm wide and 4.0 cm tall, with cones 4.6 cm across and 3.5 cm tall;

Inflorescence fragrance: Lightly honey sweet;

Flower persistence: Ray florets remaining affective in color for 10 to 14 days depending on temperatures, cone persistent and effective through drying on plant into winter;

Involucre: With numerous bracts; to about 78 per inflorescence in 4 whorls; arcuate downward toward peduncle;

Involucre bracts: Linear; narrowly acute apex; truncate base; micro-ciliolate margin; adaxial glabrous and lustrous; abaxial micro-puberulent; recurved greater than 90 degrees; average about 14.0 mm long and 3.0 mm across;

Involucre bract color: Adaxial center nearest RHS 138A and margins between nearest RHS NN137B; abaxial center and margin nearest RHS 138C;

Inflorescence buds with ray florets vertical and still enrolled: About 32.0 mm across and 30.0 mm tall; ray floret color nearest RHS 76D distally and between RHS 70A and RHS 71A proximally, with chaff portions nearest RHS 187B;

Ray florets: Zygomorphic; arrangement in single whorl, broadly-overlapping, typically imbricate; lanceolate; apex emarginated with typically two notches to 1.0 mm deep; base cuneate; margin entire; adaxial and abaxial matte and glabrous; 23 to 32 per inflorescence, typically more with initial flowering; opening to horizontal, drooping to about 30 degrees below horizontal with maturity; sterile; ligule to 40.0 mm long and 18.0 mm wide near middle, average size 38.0 mm long, 16.5 mm wide tapering to 2 mm wide in basal 3 mm; typically two thickened veins raised; twisting or enrolling absent;

Ray ligule color: When first horizontal — adaxial nearest RHS 44A, abaxial nearest RHS N155B distally and proximally nearest RHS 54D, basal 3.0 mm nearest RHS 144A; before dehiscence — adaxial between RHS 51B and RHS 50B and abaxial nearest RHS 155C with adaxial and abaxial base nearest RHS 186D;

Disc florets: About 300 to 400 per head; actinomorphic; perfect; synandrous; produced in raised dome, to about 4.6 cm across and 4.0 cm tall; individual florets to about 7.5 mm long to exserted style and 2.0 mm diameter;

Corolla: Fused forming tube; florets near outer perimeter of disc to about 7.0 mm long and 1.5 mm wide, near disc center florets about 6.0 mm long and 1.5 mm wide; fused in basal 6.0 mm, free in distal 1.0 mm; individual tepals about 0.7 mm wide at fusion; acute apex; entire margin; adaxial and abaxial surfaces slightly lustrous;

Corolla tube color: Adaxial and abaxial nearest RHS 183A in distal 2.0 mm, adaxial and abaxial proximal 5.0 mm nearest RHS 169B;

Disk floret androecium: Five; synandrous;

Staminal column: About 1.0 mm wide and protrudes from corolla tube about 1.5 mm; five connate stamens;

Anthers: Fused, about 3.0 mm long and 0.7 mm diameter; color nearest RHS 200A;

Filaments: Five; attached to column; thin, about 0.1 mm diameter and about 1.0 mm long; color nearest RHS 155D;

Pollen: Globose, abundant, less 0.1 mm in diameter, RHS 17B;

Gynoecium: Single; to about 7.0 mm long;

Style: About 4.0 mm long and 0.2 mm diameter; color nearest RHS 187B;

Stigma: Bifid; reflexed about 180°; about 1.5 mm long and 0.2 mm diameter; color nearest RHS 187B;

Seed: Achene; apex truncate to funiculus, with four main pappus; about 5.5 mm long and 2 mm across; funiculus about 1.0 mm across and 0.5 mm long; pappus 1.0 mm long and 0.5 mm across;

Seed color: Between RHS 199B and RHSN 199A;

Receptacle spines: One per disk florets; acicular; apex acute; base attenuate; lustrous; glabrous; to 15.0 mm long and 2.0 mm diameter;

Spine color: Adaxial and abaxial base nearest RHS 146D, middle portion nearest RHS 44A, distally nearest RHS 183B; becoming nearest RHS 183A with flower maturity and drying to nearest RHS 200A;

Culture and performance: The new plant performs well and with stiff stems remains upright even when exposed to heavy rains and high winds.

Disease and pest resistance: The new plant has not been shown to have any disease or pest resistance or susceptibility beyond that common to Coneflower plants.

I claim:

1. A new and distinct ornamental cultivar of *Echinacea* plant named 'Frankly Scarlet' as herein described and illustrated.

* * * * *